United States Patent [19]
Leonard et al.

[11] Patent Number: 5,503,556
[45] Date of Patent: Apr. 2, 1996

[54] EXTENDED DENTAL CLAMP

[76] Inventors: Lisa C. Leonard, 1989 Oro Fino Gulch; William C. R. Crane, 2074 Oro Fino Gulch, both of Helena, Mont. 59601

[21] Appl. No.: 355,858

[22] Filed: Dec. 14, 1994

[51] Int. Cl.$^6$ .................................................. A61C 5/12
[52] U.S. Cl. ................................................ 433/139
[58] Field of Search ...................................... 433/139

[56] References Cited

U.S. PATENT DOCUMENTS

| | | | |
|---|---|---|---|
| 412,622 | 1/1888 | Ivory | 433/139 |
| 827,236 | 7/1906 | Hansen | 433/139 |
| 1,166,924 | 1/1916 | Newlin | 433/139 |
| 1,970,875 | 8/1934 | Andaloro | 433/139 |
| 3,857,181 | 12/1974 | Rappaport | 433/139 |
| 4,004,345 | 1/1977 | Ely | 433/139 |
| 4,265,623 | 5/1981 | Soelberg et al. | 433/139 |
| 4,661,063 | 4/1987 | Levy | 433/139 |
| 4,773,857 | 9/1988 | Herrin | 433/138 |
| 4,787,849 | 11/1988 | Jacoby et al. | 433/139 |
| 4,986,752 | 1/1991 | Graves | 433/139 |

Primary Examiner—John J. Wilson

[57] ABSTRACT

A dental rubber dam clamp capable of isolating a tooth not capable of being clamped itself. Isolation is achieved by jaw extensions that engage and position the robber dam on the clamp and by placement of the clamp with its springy bridge toward the mesial or midline rather than distally.

4 Claims, 1 Drawing Sheet

FIG.1

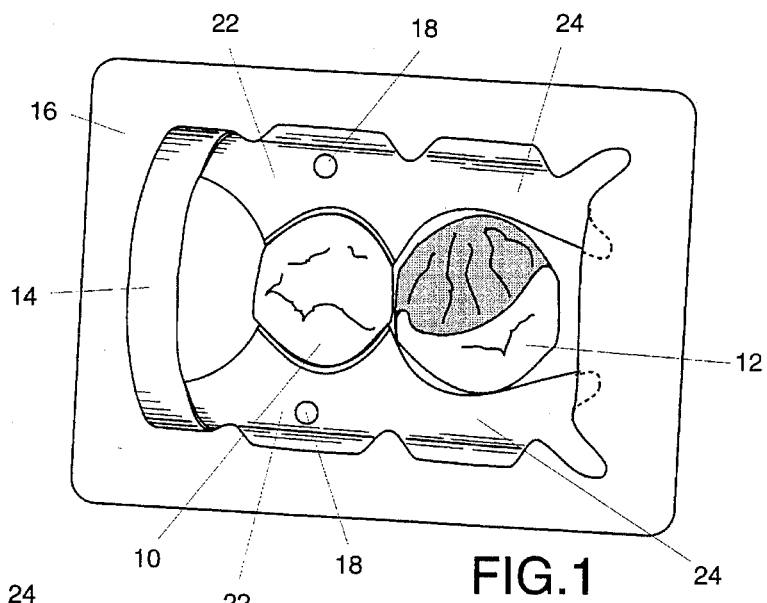
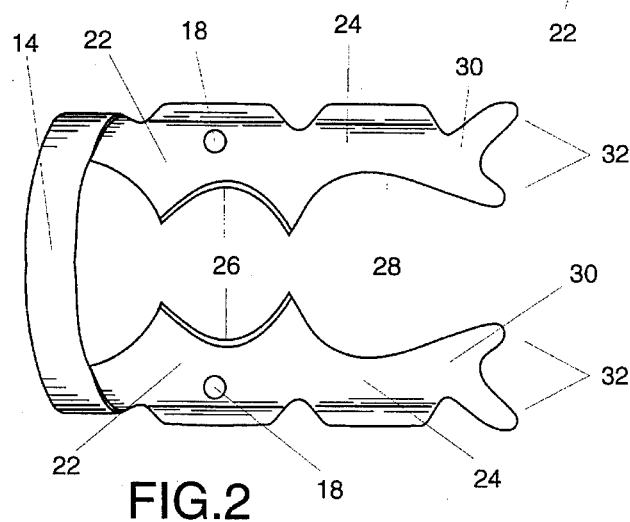
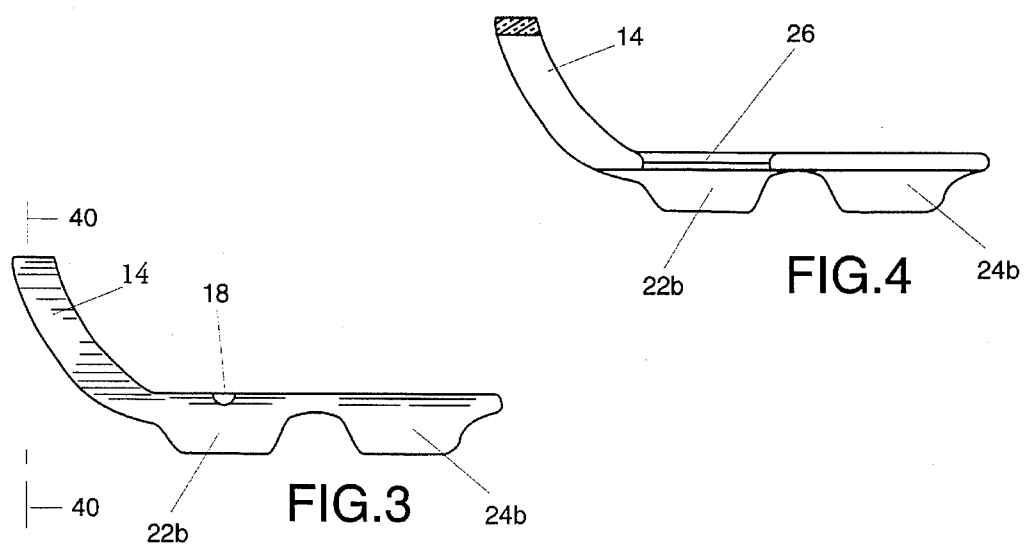

EXTENDED DENTAL CLAMP

BACKGROUND-FIELD OF THE INVENTION

This invention relates to dental instruments, specifically that of rubber dam clamps for tooth isolation.

BACKGROUND-DESCRIPTION OF PRIOR ART

There are currently numerous dental clamps on the market. There are a few patents for specialized rubber dam clamps. All of these patents have a single tooth clamp and, additionally, have a special purpose, or characteristic such as being radiotranslucent, holding back a distal flap, or permitting engagement of handling tools from many different positions.

Current clamps are placed with the springy mechanism toward the back of mouth, and subsequently the rubber dam is pulled forward or mesially. If the tooth itself cannot be clamped the flexible dental dam is typically held in place using the tooth behind the damaged tooth. There is no method or clamp currently available that enables a tooth to be isolated if it is badly broken at the gumline and has no tooth behind it. Current rubber dam and clamp designs are unusable in this situation, even if reversed, as there is no mechanism to hold and maintain the rubber dam in position behind the clamped tooth. The dam in this reversed position would slip forward and obstruct the tooth to be worked on. For this reason, when procedures are performed on this type of tooth a dam is not used, leaving no way to isolate the tooth to keep it dry and uncontaminated. When a dam is not used, there is also a possibility of losing instruments down the throat.

OBJECTS AND ADVANTAGES

Accordingly, several objects and advantages of the invention are the ability to isolate a tooth not capable of being clamped itself, keeping the same tooth dry and uncontaminated, and protecting against loss of instruments down the airway. Such a tooth would include one being broken off at the gumline, one that lacks a tooth on either side of it, or in cases where a wisdom tooth cannot be clamped itself.

The invention solves these problems by again permitting use of a rubber dam on dental procedures on any of the previously mentioned types of teeth. The dental dam serves the purpose of isolation and blocking the airway to instrument loss. The invention holds that dental dam in place.

It is also an object of this invention to provide a clamp for dental use that is specially arranged so that the customarily used instruments can be utilized with it but in an improved fashion so that the dentist's work is facilitated.

Another object of the invention is to provide a dental clamp of such a nature that, although improved, the manner of its use is apparent to a dentist without extensive extra instruction.

A further object of the invention is to provide a dental clamp that can be manufactured by the customary procedures and with only relatively inexpensive modification to the manufacturing tools.

Further objects and advantages of the invention will become apparent from a consideration of the drawings and ensuing description.

DESCRIPTION OF THE DRAWINGS

FIG. 1 is a plan of the clamp of the invention in use in a patient's mouth and engaging a flexible dental dam adjacent to two of the teeth. The dotted line indicates the the portion of the clamp hidden by the flexible dental flaxit. The shading indicates a broken portion of the tooth.

FIG. 2 is a plan view similar to FIG. 1 of the clamp by itself.

FIG. 3 is a side view of the clamp.

FIG. 4 is a view from the side and in section along the line 40—40 of FIG. 3

LIST OF REFERENCE NUMERALS

Clampable tooth
Broken or missing tooth
Springy arched bridge
Flexible rubber dam
Hole for special pliers
Multiple tips of jaws
Jaw
Lateral flange of jaw
Jaw extension
Lateral flange of extended jaw
Interior arcuate surface
Extended interior arcuate surface
Tip
Fingers of tip
Section line

SUMMARY

In summary, the invention is an improvement on currently used dental clamps by including with the jaws, an extension to engage and position the flexible dam, to permit isolation of teeth that cannot currently be isolated.

DESCRIPTION OF INVENTION

A flexible sheet rubber dam 16 is held in place by placing the present invention over a clampable tooth 10. This is typically accomplished using a special pliers that simultaneously engage opposing holes 18 to spread jaw 22. This action permits the placement of interior arcuate surfaces 26 over a clampable tooth 10. The clamp is usually of a ferrous metal containing a substantial portion of cobalt and chrome and itself is somewhat springy, although not adversely affected by autoclaving for sterilization. The clamp can also be made of plastic and be disposable. The clamp approximates a C-shape.

There is a pair of lateral jaws 22 lying substantially in a common plane and being substantially symmetrical about a longitudinal center line of the device. Each of the jaws 22 has an interior arcuate surface 26 adapted to engage the flexible rubber dam 16. Each jaw 22 includes an extension 24 which has an interior arcuate surface 28 and a tip 30 adapted to engage the flexible rubber dam 16. The tip typically includes fingers 32 which engage the rubber dam in an over under arrangement as shown in FIG. 1. In this arrangement the edge of the dam is maintained between the fingers of each jaw to keep the dam in a proper position. It is understood that alternative embodiments of the tips 30 of the jaw extensions 24 are possible that are capable of providing the function of holding and maintaining the rubber dam in a proper position at a location that is spaced from the clamped tooth. The jaws 22 and jaw extensions 24 lie roughly in the same plane. The length of the jaw extensions is roughly equivalent to the length a tooth adjacent to the clamped tooth. The jaws 22 and jaw extensions 24 may include a lateral flange 22b of jaw 22, and lateral angle 24b of extension 24 which are bent and are intended to sterile the gums. The jaws 22 are joined in a springy fashion by a springy arched bridge 14, usually integral and extended to the rear and upwardly from the general plane occupied by the jaws themselves.

OPERATION OF INVENTION

As shown in FIG. 1, a flexible sheet rubber dam 16 is perforated with small holes which are distended so as to surround a clampable tooth 10. The invention is then secured to the tooth using extended interior arcuate surface 26 with springy arched bridge 14 toward the front or mesial of the mouth. When placed in this position, extended interior arcuate surface 28 will encircle a broken tooth or the location of a missing tooth 12. The flexible rubber dam 16 is then pulled toward the back of the mouth and hooked over tips 30 of jaw extensions 24.

CONCLUSION, RAMIFICATIONS, AND SCOPE OF INVENTION

Thus, the reader will see that this invention provides a simple solution to isolate teeth in specific dental operations not previously possible, and thus protect the patient from instrument loss into the lungs, and permit the dentist an improved working environment.

We claim

1. In a clamp for clamping a tooth and for supporting a flexible sheet for isolating a second tooth during a dental operation, wherein, the second tooth is not desirably clamped or cannot be directly clamped and is adjacent the clamped tooth, said clamp comprising;

two spaced oppositely disposed jaws, and a resiliently deformable bridge connecting said jaws and serving to urge the jaws into contact with said clamped tooth;

the improvement comprising, jaw extensions extending beyond the clamped tooth and being substantially coplanar with said jaws, the jaw extensions including flexible sheet engagement means for engaging the flexible sheet at a position spaced opposite the bridge from the clamped tooth, and for maintaining the flexible sheet in a position to isolate said second adjacent tooth once engaged.

2. The clamp of claim 1, wherein the jaw extensions are substantially coplanar with the jaws.

3. The clamp of claim 1, wherein the jaw extensions include fingers that engage the flexible sheet.

4. The clamp of claim 1, wherein the jaw extensions extend beyond the clamped tooth a distance roughly equivalent to the length of a tooth adjacent the clamped tooth.

* * * * *